(12) United States Patent
Schmidt et al.

(10) Patent No.: US 9,381,091 B2
(45) Date of Patent: Jul. 5, 2016

(54) METHOD OF FIXING FIRST AND SECOND BONES USING AN IMPLANT

(71) Applicant: TriMed, Inc., Santa Clarita, CA (US)

(72) Inventors: Gary J. Schmidt, Glendale, MO (US); Jamie Riley, St. Louis, MO (US)

(73) Assignee: TRIMED, INC., Santa Clarita, CA (US)

( * ) Notice: Subject to any disclaimer, the term of this patent is extended or adjusted under 35 U.S.C. 154(b) by 0 days.

(21) Appl. No.: 13/889,930

(22) Filed: May 8, 2013

(65) Prior Publication Data

US 2013/0304224 A1 Nov. 14, 2013

Related U.S. Application Data

(60) Provisional application No. 61/644,253, filed on May 8, 2012.

(51) Int. Cl.
*A61F 2/42* (2006.01)
*A61F 2/46* (2006.01)
(Continued)

(52) U.S. Cl.
CPC .............. *A61F 2/4202* (2013.01); *A61F 2/4606* (2013.01); *A61B 17/86* (2013.01); *A61F 2002/2835* (2013.01); *A61F 2002/3021* (2013.01); *A61F 2002/30204* (2013.01); *A61F 2002/30217* (2013.01); *A61F 2002/30219* (2013.01); *A61F 2002/30622* (2013.01); *A61F 2002/30688* (2013.01); *A61F 2002/30772* (2013.01); *A61F 2002/30782* (2013.01); *A61F 2002/30784* (2013.01); *A61F 2002/30807* (2013.01); *A61F 2002/4207* (2013.01); *A61F 2002/4217* (2013.01); *A61F 2002/4223* (2013.01)

(58) Field of Classification Search
CPC ......... A61F 2/42; A61F 2/4202; A61F 2/426; A61F 2/44; A61F 2/4455; A61F 2/446; A61F 2/4465; A61F 2/447
USPC .......... 623/16.11, 17.11, 17.16, 18.11, 21.11, 623/21.12, 21.14, 21.18; 606/62
See application file for complete search history.

(56) References Cited

U.S. PATENT DOCUMENTS 5,645,598 A * 7/1997 Brosnahan, III ........... 623/17.11
5,976,187 A 11/1999 Richelsoph
(Continued)

FOREIGN PATENT DOCUMENTS

WO WO-99/38463 A2 8/1999
WO WO-00/66045 A1 11/2000

OTHER PUBLICATIONS

International Search Report and Written Opinion for PCT/US2013/040135, mailed Jul. 24, 2013.
(Continued)

*Primary Examiner* — Marcia Watkins
(74) *Attorney, Agent, or Firm* — Wood, Phillips, Ratz, Clark & Mortimer

(57) ABSTRACT

An implant for fixation of first and second bones having a body with first and second axially spaced ends and an outer surface at least nominally matched to a tapered surface around a receptacle formed by rotating a cutting element around an axis. As the body is advanced along the central axis into an operative position within the receptacle, the body outer surface and tapered surface cooperate to cause the central and second axes to consistently substantially align. A plurality of openings in the body each accepts a fastener.

47 Claims, 6 Drawing Sheets

(51) Int. Cl.
    *A61F 2/30* (2006.01)
    *A61F 2/28* (2006.01)
    *A61B 17/86* (2006.01)

(56) References Cited

U.S. PATENT DOCUMENTS

| | | | |
|---|---|---|---|
| 6,136,032 A * | 10/2000 | Viladot Perice et al. | 623/21.18 |
| 6,179,839 B1 * | 1/2001 | Weiss et al. | 606/281 |
| 6,849,093 B2 * | 2/2005 | Michelson | 623/17.15 |
| 2003/0199983 A1 * | 10/2003 | Michelson | 623/17.16 |
| 2004/0102848 A1 | 5/2004 | Michelson | |
| 2004/0127901 A1 | 7/2004 | Huebner et al. | |
| 2004/0220673 A1 * | 11/2004 | Pria | 623/19.12 |
| 2005/0010304 A1 * | 1/2005 | Jamali | 623/23.46 |
| 2005/0165484 A1 * | 7/2005 | Ferree | 623/17.11 |
| 2005/0177243 A1 | 8/2005 | Lepow et al. | |
| 2005/0216082 A1 * | 9/2005 | Wilson et al. | 623/17.11 |
| 2006/0167555 A1 | 7/2006 | Heck et al. | |
| 2008/0015587 A1 * | 1/2008 | Munoz | 606/62 |
| 2008/0154374 A1 | 6/2008 | Labrom | |
| 2008/0208349 A1 | 8/2008 | Graser | |
| 2009/0254189 A1 * | 10/2009 | Scheker | 623/21.11 |
| 2010/0023068 A1 * | 1/2010 | Bouttens et al. | 606/86 R |
| 2010/0121324 A1 * | 5/2010 | Tyber et al. | 606/62 |
| 2011/0213367 A1 | 9/2011 | Tyber et al. | |
| 2013/0006379 A1 * | 1/2013 | Jones | 623/21.18 |
| 2014/0249638 A1 * | 9/2014 | Winslow et al. | 623/19.11 |
| 2014/0257499 A1 * | 9/2014 | Winslow et al. | 623/19.13 |

OTHER PUBLICATIONS

International Preliminary Report on Patentability and Written Opinion of the Int'l Searching Authority, PCT/US2013/040135, Nov. 20, 2014.

Supplementary Partial European Search Report, issued on Dec. 14, 2015, in EP 13 78 7306.

Extended European Search Report, issued Mar. 17, 2016, in European Patent Application No. 13 787 306.3.

* cited by examiner

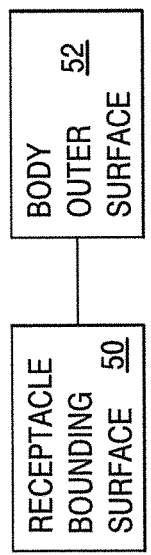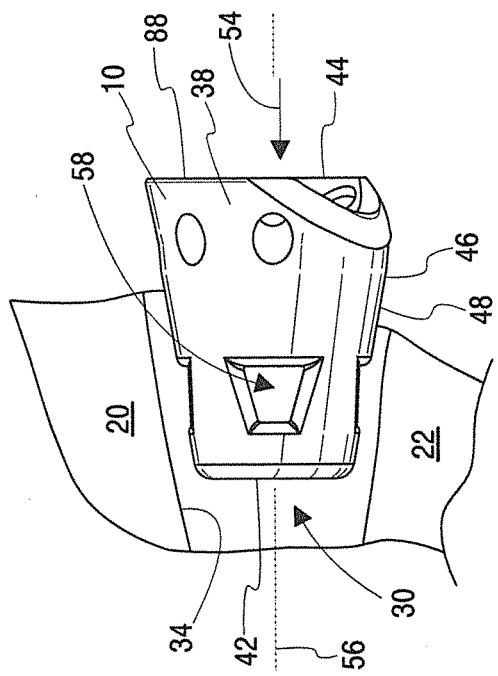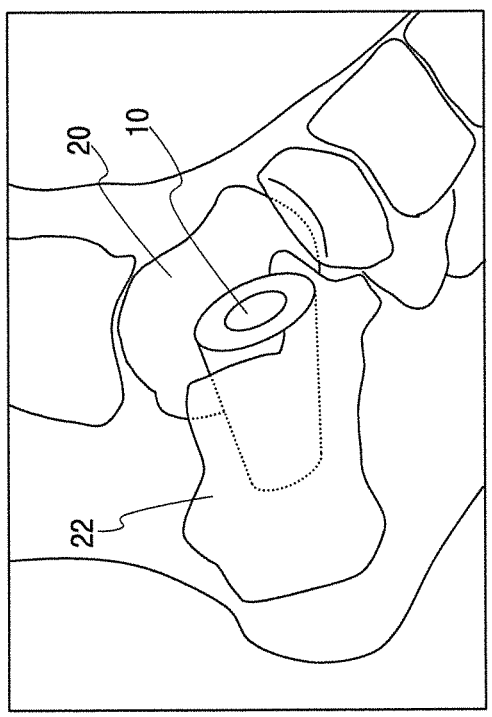

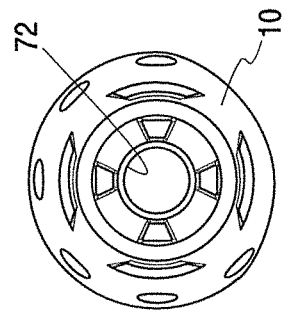
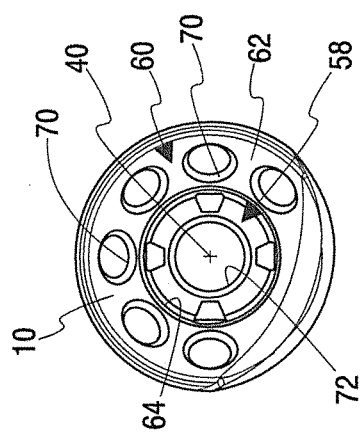
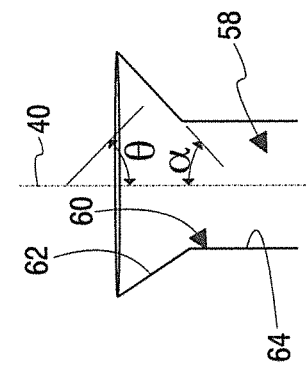
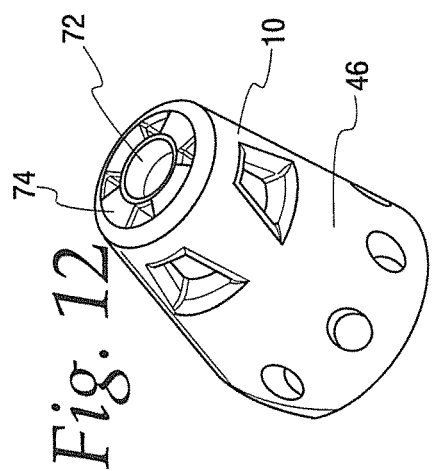
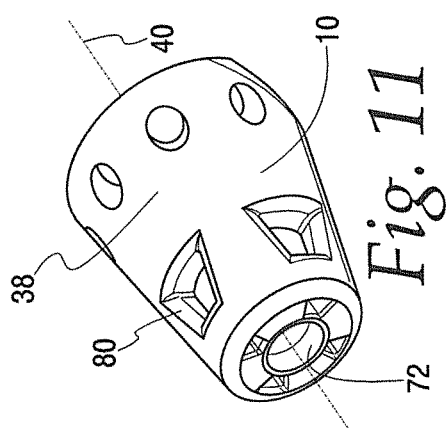
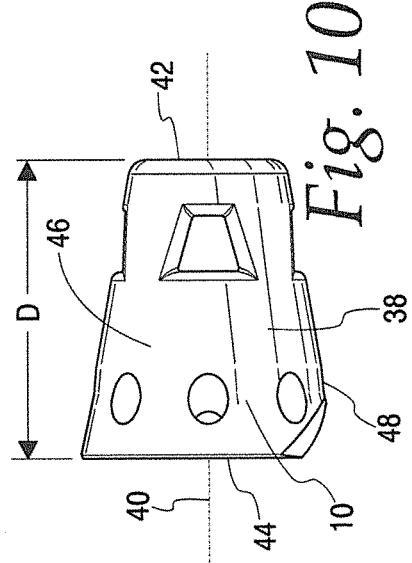

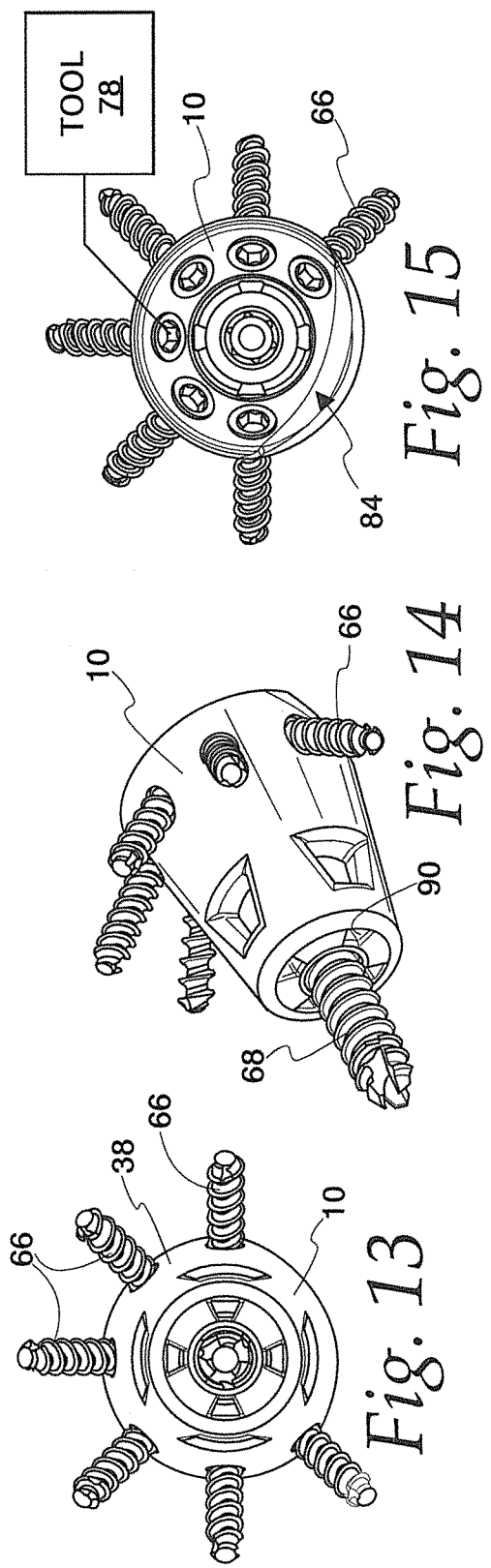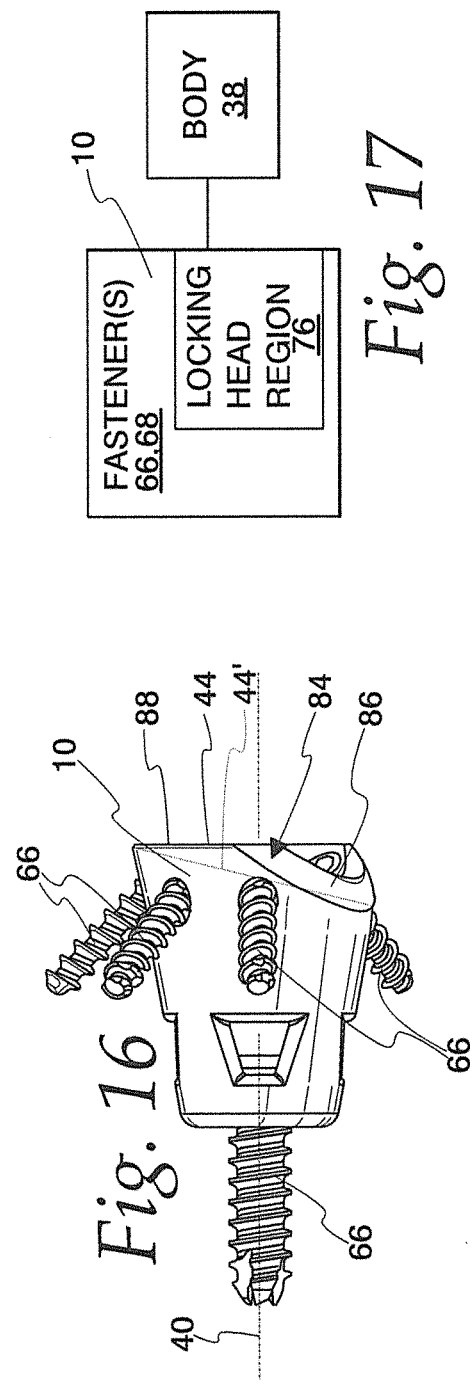

METHOD OF FIXING FIRST AND SECOND BONES USING AN IMPLANT

BACKGROUND OF THE INVENTION

1. Field of the Invention

This invention relates to implants and, more particularly, to an implant for fixation of first and second bones, as to allow fusion therebetween. The invention is also directed to a method of fixing first and second bones using the implant.

2. Background Art

It is known to fuse the talus and the calcaneus (the "heel bone") to address certain foot conditions. The talus sits on top of the calcaneus. Superiorly (on its upper surface), the talus forms a major part of the ankle joint, this joint providing the motion that allows the foot to go up and down. Inferiorly (on its lower surface), the talus forms a separate joint with the calcaneus, the subtalar joint. The subtalar joint is actually not a single joint surface but rather formed by three separate and distinct facets, with the posterior facet being the major part and the anterior and middle facets small contributions to this joint. The three joints work together, however, and provide the motion that allows the heel to invert or evert from side to side so that the foot can maintain a flat contact with uneven ground.

On the lateral side of the hindfoot between the posterior facet and the other facets of the subtalar joint (middle, anterior), there is a conical shaped interval between the talus and the calcaneus. This cone of soft tissue between the two bones is called the sinus tarsi. It is wider laterally and tapers medially as it crosses between the two bones.

Certain conditions such as fractures of the calcaneus or flat feet can lead to arthritis of the subtalar joint, which can cause considerable pain and dysfunction with walking. When this is not controlled with simple methods of treatment, such as anti-inflammatory medication or shoe inserts, a preferred treatment can be to perform arthrodesis, or fuse, the subtalar joint. Although arthrodesis creates a single bone between the talus and calcaneus and eliminates all motion between the two bones, it can be very effective for controlling pain.

The general principles of arthrodesis or fusing a joint are no different when addressing the subtalar joint as compared to any other joint. The surface cartilage is removed and the bone roughened on the joint surfaces to create a surface that is conducive to causing the bones on either side to heal to one another. Frequently, this includes the application of bone graft, or porous cancellous bone that is removed and applied across the surfaces of the joint. In a simplistic way of looking at this, the surgeon is trying to get the bone on each side of the joint to 'think' it has been fractured so that they heal to one another.

In addition to preparation of the joint surface and application of bone graft, it is important to stabilize the joint to eliminate micromotion between the two bones while healing takes place. This helps to prevent disruption of the microscopic crossing channels of bone that are laid down during the healing phase, a process that prevents the two bones from healing to one another.

There are different methods that are currently used to rigidly fix the two bones in order to promote arthrodesis of the subtalar joint.

One method is to apply a plate across the surface of the two bones. Plate fixation has the disadvantage of requiring a large incision to allow application of a plate large enough to provide fixation. The skin in this area is frequently thin and has a poor vascular supply, and large incisions are prone to breakdown, dehiscence, and infection. In addition, since plates are applied to the surface of the bone, they need to be thick enough to withstand the relatively large loads from bending torque; this bulk can contribute to skin breakdown or irritation.

Another method is to place screws across the joint. Simple screw fixation, however, is not a strong method of fixation and may fail with the loads that are applied with weight bearing.

Still another method of fixation is to place staples across the joint. Since staples are on the surface of the bone they are subject to bending torque and can loosen. In addition, staples only fix a single surface of the joint which limits fixation across the joint surface.

All current methods of fixation are deficient in one or more respects, as described above. Many of the methods apply implants to the surfaces of the bone which are at significant distances from the joints being fused; these are less effective at controlling micromotion across the joint surfaces and are subject to considerable cantilever bending loads. In addition, these methods require direct tedious intraarticular debridement of the joint surface with extensive exposures in order to expose raw bone surfaces on either side of the joint.

Those in the medical art continue to seek out better methods of fixation of bones, particularly at the subtalar joint.

SUMMARY OF THE INVENTION

In one form, the invention is directed to an implant for fixation of first and second bones at a first site. The implant consists of a body having a central axis and a depth dimension between first and second axially spaced ends. The body has an outer surface at least nominally matched to a tapered surface around a receptacle formed at the first site by rotating a cutting element around a second axis. The body outer surface and tapered surface are configured so that as the body is advanced along the central axis into an operative position within the receptacle, the body outer surface and tapered surface cooperate to cause the central and second axes to consistently substantially align. A plurality of openings in the body each accepts a fastener. The plurality of openings consists of: a) a first opening through which a first fastener can be directed along a first line through the operatively positioned body and into one of the first and second bones; and b) a second opening through which a second fastener can be directed along a second line through the operatively positioned body and into one of the first and second bones.

In one form, the implant is used in combination with a reamer for defining the bore at the first site. The reamer has a central axis and is configured to produce a truncated conical shape for at least a portion of the tapered surface as an incident of the reamer turning around its central axis.

In one form, the first opening is formed so that the first fastener can be advanced into one of the first and second bones in a line substantially parallel to the central axis of the body.

In one form, one of the openings is formed so that one of the fasteners can be advanced therethrough in one of the first and second lines that is non-parallel to the central axis of the body.

In one form, the second opening is formed so that the second fastener can be advanced into one of the first and second bones along the second line that is at an angle to the central axis of the body.

In one form, the first and second lines are not parallel to each other.

In one form, the first and second lines are non-parallel to the central axis of the body.

In one form, at least a portion of the outer surface of the body has a truncated conical shape.

In one form, the body has a central cavity with a non-uniform diameter.

In one form, the first end of the body is a leading end as the body is advanced into the operative position. The central cavity is bounded by a ring-shaped inner surface portion through which one of the openings is formed.

In one form, the ring-shaped inner surface portion extends over less than half of the depth dimension between the first and second axial ends of the body and blends axially into a second inner surface portion that has a shape that is different than a shape of the ring-shaped inner surface portion.

In one form, the ring-shaped inner surface portion is at an angle to the central axis of the body that is greater than an angle at which the second inner surface is at relative to the central axis of the body.

In one form, the second inner surface portion terminates at an axially facing wall.

In one form, one of the openings is formed in the axially facing wall.

In one form, the body has a peripheral wall defining the outer surface. There is at least one discrete receptacle formed in the outer surface to create a volume for bone graft material between the operatively positioned body and one of the bones.

In one form, the body has a central cavity bounded by a peripheral wall. There is at least one opening through the peripheral wall to allow placement of a volume of bone graft material that is contiguous through the at least one opening between one of the first and second bones and the central cavity.

In one form, the at least one opening is a plurality of openings that allow placement of a volume of bone graft material that is contiguous through the plurality of openings and central cavity between each of the first and second bones.

In one form, the body has a peripheral wall. The peripheral wall has a discrete truncation extending only partially around the central axis at the first end.

In one form, the body consists of one of: a) a thermoplastic material; and b) a thermoplastic material that is polyether ether ketone (PEEK).

In one form, the first and second openings each has an entryway that is spaced along the central axis from each of the first and second body ends.

In one form, the first end of the body is a leading end defined by a leading surface and the second end of the body is a trailing end defined by a trailing surface. The trailing surface has at least a portion thereof that is not perpendicular to the central axis of the body.

In one form, the implant is provided in combination with the first and second fasteners.

In one form, at least one of the fasteners is a polyaxial locking screw.

In one form, at least one of the fasteners has a head region that is threadably locked to the body.

In one form, the invention is directed to an implant for fixation of first and second bones at a first site. The implant consists of a body having a central axis and a depth dimension between first and second axially spaced ends. The body has an outer surface at least nominally matched to a tapered surface around a receptacle formed at the first site by rotating a cutting element around a second axis. The body outer surface and tapered surface are configured so that as the body is advanced along the central axis into an operative position within the receptacle, the body outer surface and tapered surface cooperate to cause the central and second axes to consistently substantially align. There are a plurality of openings in the body to each accept a fastener. The plurality of openings consists of: a) a first opening through which a first fastener can be directed along a first line that is substantially parallel to the central axis of the body and into one of the first and second bones; and b) a second opening through which a second fastener can be directed along a second line into one of the first and second bones.

In one form, the second line is at an angle to the first line.

In one form, the body has a central cavity bounded by a peripheral wall. There is at least one opening through the peripheral wall to allow placement of a volume of bone graft through the at least one opening between one of the first and second bones and the central cavity.

In one form, the body has a peripheral wall defining the outer surface. There is at least one discrete receptacle formed in the outer surface to create a localized volume for bone graft material between the operatively positioned body and one of the bones.

In one form, the invention is directed to a method of fixing first and second bones. The method includes the steps of: providing the implant as described above; forming a receptacle bounded by a tapered surface at the first site through parts of the first and second bones; directing the first end of the body into the receptacle to operatively position the body; directing a first fastener through the first opening into one of the first and second bones; and directing a second fastener through the second opening into one of the first and second bones.

In one form, the step of forming a receptacle involves forming a receptacle using a reamer with a central axis by rotating the reamer around its central axis.

In one form, the step of forming a receptacle involves forming a receptacle by removing bone material on each of the first and second bones.

In one form, the step of forming a receptacle involves forming a receptacle with a reamer that produces a conical shape for the tapered surface bounding the receptacle.

In one form, the step of providing an implant involves providing an implant wherein the outer surface of the body has a conical shape at least nominally matched to the conical shape for the tapered surface bounding the bore.

In one form, the step of directing the first end of the body into the receptacle involves pressing the body into the operative position by exerting a force on the body along the central axis of the body and without turning the body around the central axis of the body.

In one form, the first and second bones are a patient's talus and calcaneus bones.

In one form, the step of forming a receptacle involves forming a receptacle at the patient's sinus tarsi.

In one form, the step of providing an implant involves providing an implant wherein the body has at least one recess at the outer surface to thereby create a volume between the body and one of the first and second bones within the bore. The method further includes the step of placing bone graft material in the recess.

In one form, the receptacle has a bottom. The step of directing the first end of the body into the receptacle involves causing the outer surface of the body to wedge against the tapered surface of the receptacle with the first end of the body spaced from the bottom of the receptacle.

In one form, the method further includes the steps of directing one of the fasteners through the first end of the body and into one of the bones and repositioning the one fastener to thereby forcibly draw the outer surface of the body and the tapered surface of the bore against each other.

In one form, the step of providing an implant involves providing an implant wherein the body has a central cavity bounded by a peripheral wall with an opening through the peripheral wall. The method further includes the step of placing bone graft so that a contiguous volume of the bone graft extends from the central cavity through the opening in the peripheral wall and to against one of the bones.

In one form, the step of providing an implant involves providing an implant wherein the body has a ring-shaped surface through which the first and second openings extend. The step of directing the first and second fasteners involves of directing the first and second fasteners through the ring-shaped surface along the first and second lines that are non-parallel to the central axis of the body.

In one form, the step of providing an implant involves providing an implant wherein the body has a third opening. The method further includes the step of directing a third fastener along the central axis of the body through the third opening and into one of the bones.

BRIEF DESCRIPTION OF THE DRAWINGS

FIG. 4 is a fragmentary, perspective view of a part of the foot in FIG. 3 with the implant in FIG. 3 shown in schematic form and fixed in place at the subtalar joint;

FIG. 5 is a schematic representation of cooperating surfaces on the inventive implant and bones at an implant site;

FIG. 6 is an enlarged, side elevation view of the implant in FIG. 3 with a body thereon being directed into an operative position within a receptacle defined at the subtalar joint;

FIG. 7 is a schematic representation of a surface bounding a central cavity on the implant in FIG. 6;

FIG. 8 is an end elevation view of the implant as shown in FIG. 6;

FIG. 9 is an elevation view of the implant from the end opposite that in FIG. 8;

FIG. 10 is an elevation view of the implant from the side opposite that in FIG. 6;

FIG. 11 is a perspective view of the implant as shown in FIGS. 6-10;

FIG. 12 is a view of the implant taken from a perspective different than that in FIG. 11;

FIG. 13 is a view as in FIG. 9 wherein fasteners for the implant are directed through the implant;

FIG. 14 is a view as in FIG. 11 with the fasteners in place;

FIG. 15 is a view as in FIG. 8 with the fasteners in place;

FIG. 16 is a view as in FIG. 6 with the fasteners in place;

FIG. 17 is a schematic representation of fasteners of the type shown in FIGS. 13-16, for securing the implant to bone;

DETAILED DESCRIPTION OF THE PREFERRED EMBODIMENT

Figure 1:
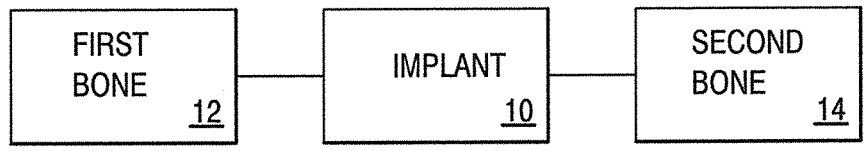
FIG. 1 is a schematic representation of an implant for fixation of first and second bones at any site on a human body, according to the invention.

In FIG. 1, there is a generic showing of the inventive implant 10 used to fix first and second bones 12, 14, respectively. The implant 10 and bones 12, 14 are shown schematically to cover the full breadth of the invention. The schematic showing of the implant 10 is intended to encompass all versions, as described herein, and virtually an unlimited number of variations thereof that would be apparent to one skilled in the art from the disclosure herein. The first and second bones 12, 14 are shown schematically to include specific bones for which the implant 10 is particularly adapted, as described hereinbelow, and bones at any site in the human body that might be fixed consistently with the principles described herein.

Figure 2:
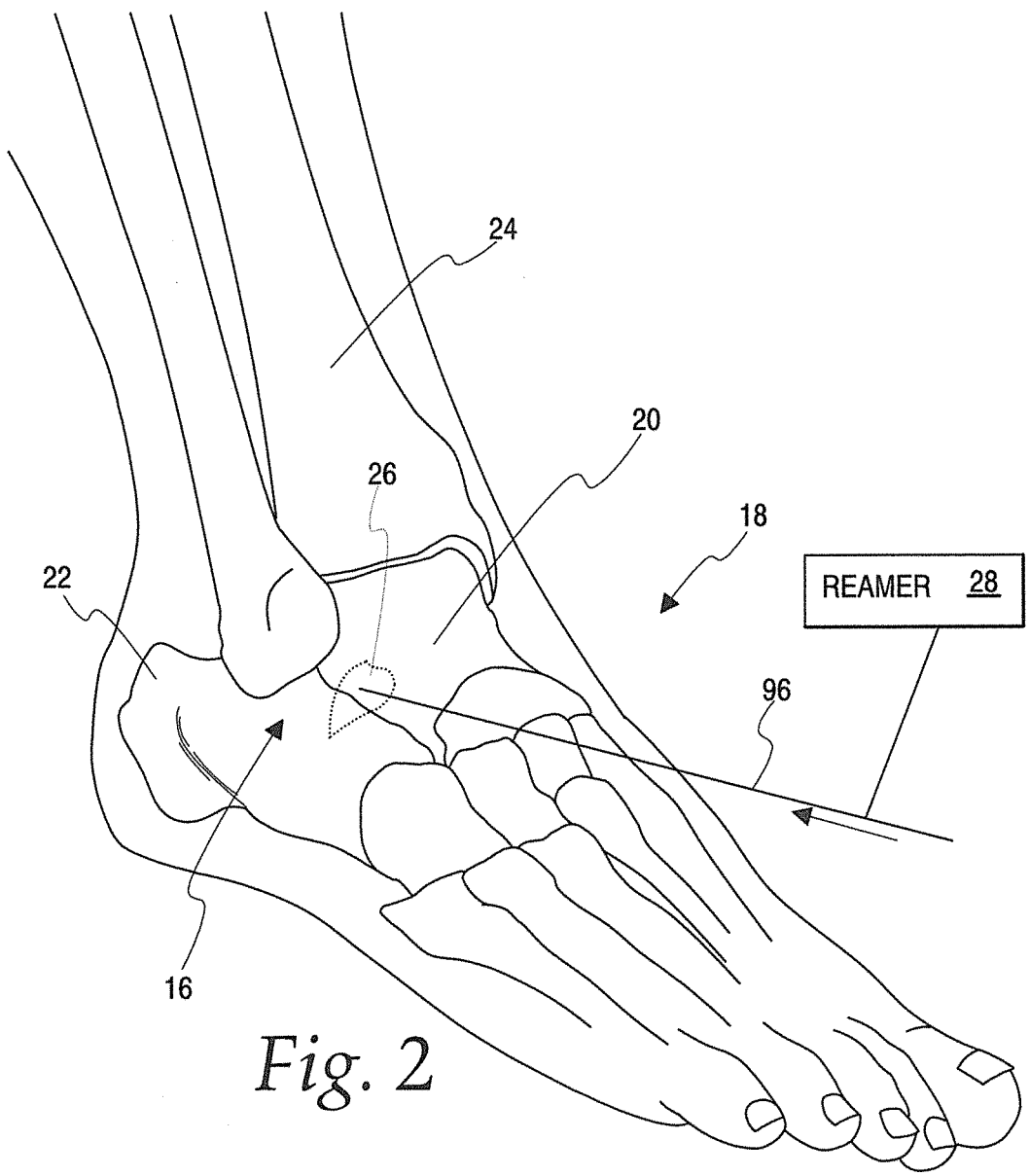
FIG. 2 is a perspective view of a patient's lower leg and foot and showing talus and calcaneus bones which may be fixed relative to each other using the inventive implant.
Figure 3:
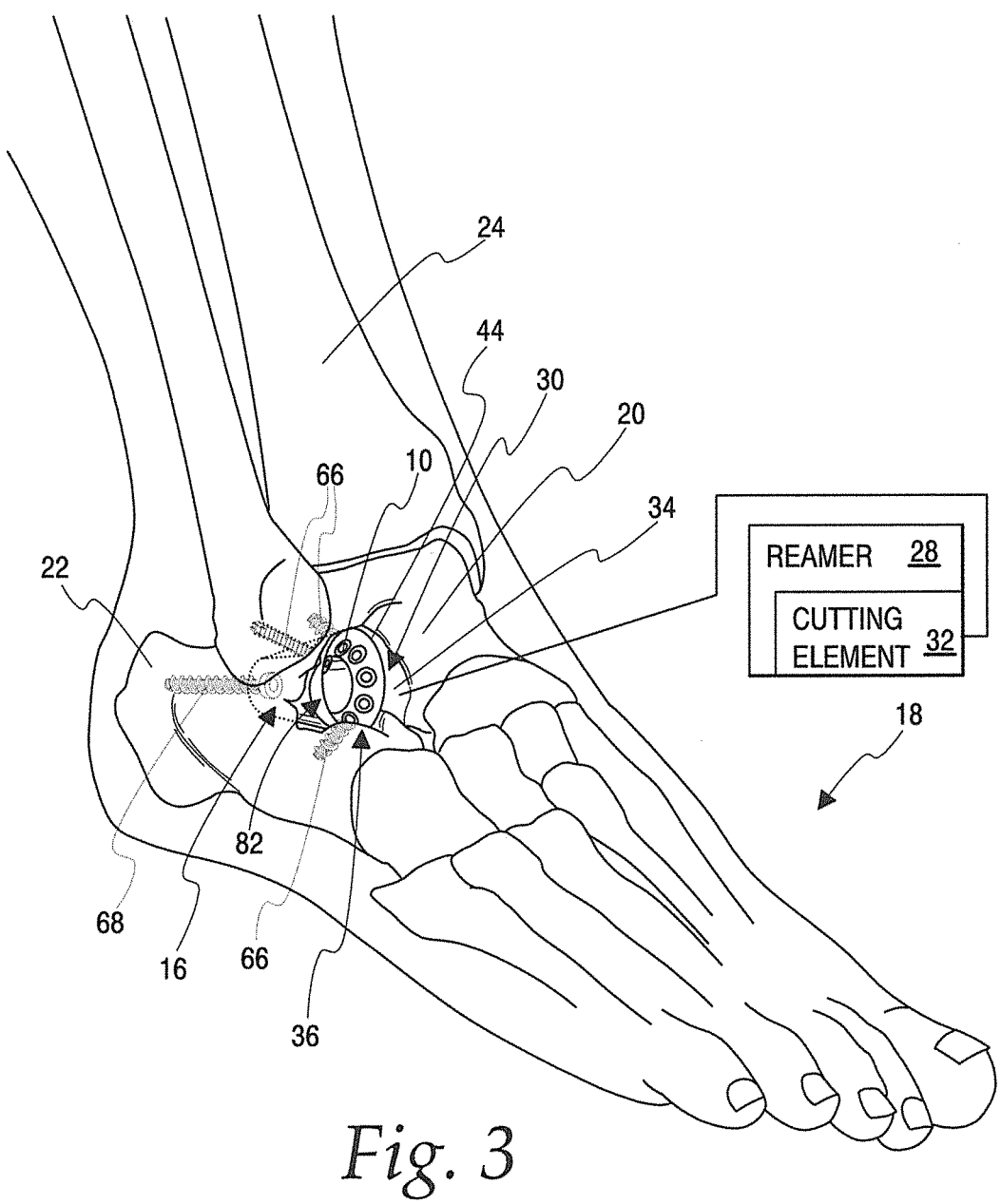
FIG. 3 is a view as in FIG. 2 with one specific form of implant, according to the present invention and as shown schematically in FIG. 1, in place at the subtalar joint and secured with fasteners.

The invention will be described herein as used at the subtalar joint at 16 on a human foot at 18, as shown in FIGS. 2-4. The subtalar joint 16 is located where the talus 20 sits on top of the calcaneus 22. The tibia 24 is situated on top of the talus 20. A conical region of soft tissue, called the sinus tarsi 26, resides between the talus 20 and calcaneus 22. This mass of tissue is wider laterally and tapers medially so as to produce the aforementioned conical shape.

One specific form of implant 10, and method of fixing the talus 20 and calcaneus 22 using the same, will now be described with respect to FIGS. 2-18.

As shown in FIGS. 2 and 3, a conventional reamer 28 is shown for producing a receptacle at 30 for the implant 10. The reamer 28 may take any conventional form. Typically, the reamer 28 will have a cutting element 32 that rotates around an axis to produce a surface 34 at the implant site 36 with a diameter that increases from the leading end of the cutting element 32 in a trailing direction. Preferably, the cutting element 32 is configured so that the receptacle 30 formed thereby is configured by eliminating a substantial portion, if not all, of the sinus tarsi 26. The resulting tapered surface 34 is defined in part by the talus 20 and calcaneus 22.

The implant 10 has a body 38 with a central axis 40 and a depth dimension D between a first axial end 42 and a second axial end 44. The body 38 has a peripheral wall 46 that extends around the central axis 40 and defines an outer surface 48. The outer surface 48 is at least nominally matched to the shape of the surface 34 bounding the formed receptacle 30.

FIG. 5 is a schematic representation of a cooperating receptacle bounding surface 50 and body outer surface 52 which generically represent the surfaces 34, 48, specifically described herein, and other cooperating surface configurations contemplated. For example, as explained in greater detail below, the depicted surfaces 34, 48 have cooperating conically-shaped regions. While this is one preferred form, the invention contemplates virtually any cooperating tapered surfaces 50, 52 that are configured so that as the body 38 is advanced along its axis 40 in the direction of the arrow 54 in FIG. 6 into its operative position within the receptacle 30, as shown in FIG. 3, the surfaces 50, 52 cooperate to cause the axes thereof to consistently substantially align. In a preferred embodiment, the central axis 40 of the body 38 will consistently substantially align with the central axis 56 of the receptacle 34 formed by the reamer 28.

As just examples, the implant might have a body with a parabolic outer surface. Alternatively, the shape of the outer surface of the body may have significant deviations from a shape traced continuously around the implant axis. The interruptions in the surface may allow for placement of bone graft material, as described herein. As just one example, the implant outer surface might be formed by a pair of diametrically opposite ribs with tapering surfaces nominally matched to the configuration of the tapering surface bounding the implant receptacle.

While the conical shape of the surfaces, including the truncated conical shape of the surface 34 bounding the receptacle 30 and the truncated conical shape of the outer surface 48 of the body 38, is a preferred shape, the selection of this shape for description herein should not be viewed as limiting.

The peripheral wall 46 of the body 38 extends around a central cavity 58 shown with a non-uniform diameter. The central cavity 58 is bounded by an inner surface 60 with a ring-shaped inner surface portion 62 adjacent to the second/trailing end of the body 38. The ring-shaped surface portion 62 preferably extends over less than one-half the depth dimension D of the body and transitions axially into a second inner surface portion 64 that has a shape that is different than the shape of the ring-shaped surface portion 62.

More particularly, as may be seen most clearly in FIG. 7, which schematically shows the shape of the surface 60, the ring-shaped surface portion 62 at any circumferential location makes an angle α with respect to the central axis 40 of the body 38. The angle α is substantially greater than the angle that the surface portion 64 makes with respect to the axis 40. In the particular embodiment, the surface portion 64 is substantially parallel (at zero degree angle) with respect to the central axis 40. A slight tapering or other shape is also contemplated. The surface portion 62 may be straight at any circumferential location, or potentially slightly curved. The angular relationship of the ring-shaped surface portion 62 facilitates direction of fasteners therethrough and access to fasteners through tools, as described hereinbelow. By making the angle between the surface portion 62 and axis relatively large, fasteners can be directed therethrough in lines that are at large angles relative to the central axis 40. Room is provided for handling the fasteners and drivers therefor.

Fasteners, shown as threaded fasteners 66, 68, are utilized to fix the body 38 to the talus 20 and calcaneus 22. While in the embodiment shown, there are seven total fasteners 66, 68 utilized, the invention contemplates use of fewer, or more, of such fasteners 66, 68.

To accommodate the fasteners 66, 68, openings 70, 72 are pre-formed in the body 38. The opening 72 is provided through the leading end wall 74 to guide a fastener 68 therethrough generally in a line parallel to the central axis 40 of the body 38.

The openings 70 are circumferentially spaced around the ring-shaped surface portion 62 and are formed with their central axes angled with respect to the central axis 40, thereby to guide the fasteners 66 generally in lines at a substantial angle Θ (FIG. 7) with respect to the central axis 40 of the body 38.

In one form, the openings 70, 72 are threaded so that the fasteners 66, 68 are advanced in their respective lines at substantially a pre-determined angle.

Polyaxial locking screws may be used for the fasteners 66, 68. In one variation, the body 38, or at least the portion thereof that defines the openings 70, 72, is made out of plastic, such as a thermoplastic material. One suitable thermoplastic material is polyether ether ketone (PEEK).

The fasteners 66, 68 may be made out of metal, such as titanium. An enlarged head might be utilized to allow the fasteners 66, 68 to lock into the body 38. A schematic representation of polyaxial fasteners 66, 68 is shown in FIG. 17. In that Figure, the fasteners 66, 68 have a locking head region 76 that threadably locks with the body 38 when tightened.

As seen particularly in FIGS. 3 and 16, the fastener 68 can be directed generally parallel to the axis 40 into the calcaneus 22. The fasteners 66 can be directed angularly relative to the central axis 40 along their respective lines into the talus 20 and calcaneus 22. This causes the implant to be rigidly secured to each of the talus 20 and calcaneus 22. With this arrangement, multiple planes of insertion of the fasteners 66, 68 provides rigid connection with holding force application in multiple directions to positively secure the body 38 to the talus 20 and calcaneus 22 and thus the talus 20 and calcaneus 22 to each other. Tightening of the fasteners 66, 68 draws the talus 20 and calcaneus 22 towards each other. This compressing action promotes bone fusion.

The strategic configuration of the surface 60, including that at the ring-shaped surface portion 62, facilitates introduction of the fasteners 66 at the multiple angles. This configuration allows the openings 70 to be spaced fully from the second body end 44 significantly so as not to compromise the integrity of the body 38 thereat. At the same time, the angular relationship of the surface portion 62 creates a widened diameter whereby the fasteners 66 can be readily introduced into their respective openings 70 and manipulated without interference with an appropriate turning tool 78.

The central cavity 58 serves a number of purposes. First of all, it decreases the overall quantity of material needed to form the body 38. As noted previously, the central cavity 58 also facilitates the placement of numerous fasteners 66 at different angular relationships. The configuration of the surface portion 64 is not as critical as that of the surface portion 62. In the depicted embodiment, the second surface portion 64 extends fully to the axially facing end wall 74. The diameter of the surface portion 64 may be uniform or variable.

The body 38 is also constructed to accommodate bone graft material that can be strategically placed to enhance the fixation/fusion process. In this embodiment, four openings 80 are provided, in the depicted embodiment, at circumferentially spaced locations around the peripheral wall 46. The openings 80 each accommodates a volume of bone graft material. The openings 80 are shown fully through the peripheral wall 46 so as to allow a volume of bone graft material to be filled therein to be contiguous with the central cavity 58 and the talus 20 and calcaneus 22. By providing multiple openings 80, the volume of bone graft material can be placed to be contiguous fully through the openings 80 and central cavity 58 fully between each of the talus 20 and calcaneus 22, to effect a more positive interlock.

The openings 80 are shown to have a trapezoidal shape. This particular shape is not critical, but is desirable in that it causes a positive interlock of the bone graft material.

It is also possible to form bounded receptacles that do not extend fully through the peripheral wall 46, whereby there is localized interlocking between the outer surface 48 of the peripheral wall 46 and the adjacent bone—talus 20 or calcaneus 22.

The openings and/or receptacles are sized, shaped, and located to allow strategic placement of a volume of bone graft material to enhance bone fusion and stabilize the fused bones.

As seen in FIG. 3, with the body 38 in its operative position, a region at the second axial end 44 at 82 may project so as to potentially contact and irritate adjacent tissues. Accordingly, the body 38 is formed with a discrete truncation 84 at this location. This truncation 84 produces a generally flat surface 86 that is non-orthogonal to the central axis 40 as is the remainder of the surface 88 at the second end 44 of the body 38. This feature avoids issues of soft tissue prominence in situations in which the central axis of the receptacle is angled relative to the surface plane of the bone.

As an alternative, as shown in dotted lines in FIG. 16, the entire surface at the end 44' may be angled to eliminate that portion of the body 38 that may otherwise project so as to contact adjacent tissues.

Graft receiving openings 90 may also be provided in the end wall 74 to enhance fusion thereat.

Figure 18:
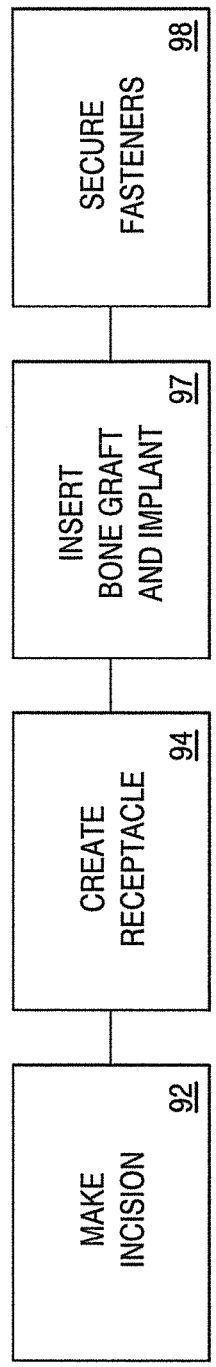
FIG. 18 is a flow diagram representation of a method of fixing first and second bones using the inventive implant.

With the above described structure, a procedure using the implant 10 can be carried out as follows, and as shown in flow diagram form in FIG. 18. An incision is made as shown at block 92 over the lateral side of the foot, centered over the sinus tarsi 26. The dissection is continued deeply, removing the soft tissue from the sinus tarsi 26 to expose the surface of the talus 20 and calcaneus 22.

As shown at block 94, the receptacle 30 is formed, as by using the aforementioned reamer 28. Typically, as shown in FIG. 2, a guide pin 96 is inserted through the sinus tarsi 26 down the subtalar joint and into the calcaneus 22. The reamer 28 is passed over the pin 96 and operated to form the receptacle 30. Of course, the receptacle 30 could be formed without using the pin 96.

The reamer operation creates a raw cancellous bone surface on either side of the joint in the talus 20 and calcaneus 22. Further removal of the cartilage of the subtalar joint can be done at this stage, and graft inserted into areas of the joint that are deep to the reamed surface 34.

Next, bone graft is applied into the receptacle, whereupon the implant 10 is inserted, as shown at block 97. The implant 10 is secured using the fasteners 66, 68, as shown at block 98.

Ideally, the major facet to the subtalar joint is the posterior facet. Fusion across the posterior facet of the subtalar joint is usually adequate to fuse the entire joint. The implant 10 is inserted through the sinus tarsi 26 and directed posteriorly across the posterior facet.

During the reaming process, the bone in the talus 20 and calcaneus 22 is shaved and creates bone graft which can be used to enhance the fusion. The opening into the subtalar joint also provides easy access to further decorticate the deeper portions of the joint to promote fusion.

The implant 10 can be pressed into place without turning the body 38 around the axis 40. By reason of the configurations of the cooperating surfaces 34, 46, the advancing implant 10 tends to coaxially align with the receptacle 30 and become wedged. The body 38 can be configured so that this wedging occurs before the end wall 74 contacts the calcaneus 22. Accordingly, by tightening the fastener 68 further, the implant 10 tends to draw the talus 20 more positively against the calcaneus 22 to produce a greater compressive action that further secures the fixation.

Figure 19:
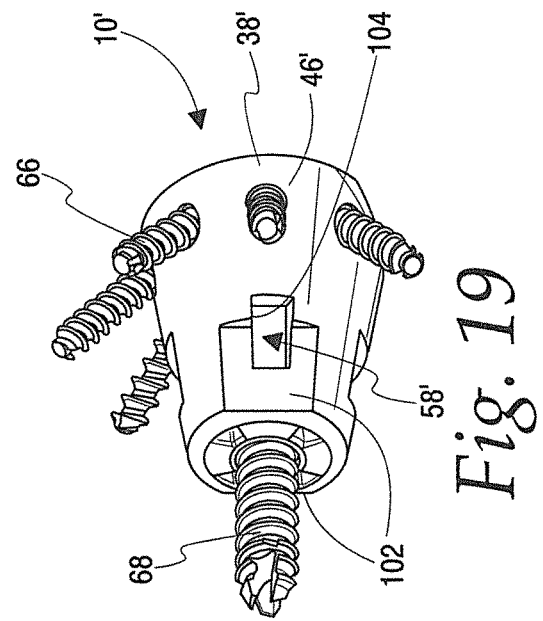
FIG. 19 is a view as in FIG. 14 and showing a modified form of implant body.

As noted previously, the precise shape of the outer surface 48 of the peripheral wall 46 is not limited to what is described above. As one other variation, as shown in FIG. 19, a modified form of implant 10' is shown with a body 38' having diametrically opposite flats 102 thereon. The flats 102 coincide with openings 104 through the peripheral wall 46' that are contiguous with the central cavity 58'. The flats 102 produce receptacles to contain a volume of bone graft between the body 38' and the adjacent bone—talus 20 or calcaneus 22. The implant 10' in all other respects may be the same as the implant 10, described above, and fixed using the fasteners 66, 68.

There are several potential advantages realized using the inventive implant and method.

First, only a limited incision is needed over the sinus tarsi, since wide exposure of the lateral surfaces of the talus and calcaneus is not needed (such as with application of a plate or even staples). This avoids problems with wound breakdown, reduces the risk of infection, and avoids large scars.

Second, preparation of the joint surface for fusion may be simplified. A conical reamer allows preparation of a surface for intimate apposition of the surface of the implant to the bone, and prepares a raw bone surface that promotes fusion. This can be accomplished without the wide exposure and tedious debridement of the individual joint surfaces.

Third, the conical structure of the implant is an extremely strong geometric shape that is capable of withstanding the large loads applied across the subtalar joint. Unlike staples, screws or plates, this implant is loaded in nearly pure compression and, like a dome of a building or arch of a bridge, distributes the load evenly across the entire surface.

Fourth, screw fixation through the implant may securely fix the implant to the bone.

Finally, surface relief in the implant and windows allow the fusion mass to cross the joint.

The foregoing disclosure of specific embodiments is intended to be illustrative of the broad concepts comprehended by the invention.

The invention claimed is:

1. A method of fixing first and second bones at a first site, the method comprising the steps of:
   a) providing an implant comprising:
      a body having a central axis and a depth dimension between first and second axially spaced ends,
      the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion,
      a diameter of the ring-shaped inner surface portion greater than a diameter of the second inner surface portion,
      the ring-shaped inner surface portion extending less than one half the depth dimension of the body,
      a plurality of openings in the body each to accept a fastener,
      the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;
   b) forming a receptacle at the first site bounded by a tapered surface at the first site through parts of at least one of the first and second bones, the receptacle having a central axis,
      the body outer surface at least nominally matched to the tapered surface,
      the body outer surface and tapered surface configured so that as the body is advanced along the central axis of the receptacle into an operative position within the receptacle, the body outer surface and tapered surface cooperate to cause the central axis of the receptacle and second axis to consistently substantially align,
   c) directing the first end of the body into the receptacle to operatively position the body;
   d) directing the first fastener through the first opening in the first line into one of the first and second bones; and
   e) directing the second fastener through the second opening in the second line into one of the first and second bones,
   at least one of the first and second fasteners extending through the ring-shaped inner surface portion and not the second inner surface portion,
   wherein the step of providing an implant comprises providing the implant wherein the first and second openings extend through the ring-shaped surface and the steps of directing the first and second fasteners comprise directing the first and second fasteners through the ring-shaped surface along the first and second lines that are non-parallel to and non-coincident with the central axis of the body, the method further comprising the step of directing the other of the first and second fasteners through the body at a location spaced from the ring-shaped inner surface portion.

2. The method of fixing first and second bones according to claim 1 wherein the other of the first and second fasteners is directed through the body in a line substantially parallel to or coincident with the central axis of the body.

3. The method of fixing first and second bones according to claim 2 wherein the one of the first and second fasteners is directed into one of the first and second bones and the other of the first and second fasteners is directed into the other of the first and second bones to threadably engage the other of the first and second bones to thereby axially draw the first and second bones towards each other along the central axis of the body.

4. A method of fixing first and second bones at a first site, the method comprising the steps of:
a) providing an implant comprising:
a body having a central axis and a depth dimension between first and second axially spaced ends,
the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion,
a diameter of the ring-shaped inner surface portion greater than a diameter of the second inner surface portion,
the ring-shaped inner surface portion extending less than one half the depth dimension of the body,
a plurality of openings in the body each to accept a fastener,
the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;
b) forming a receptacle at the first site bounded by a tapered surface at the first site through parts of at least one of the first and second bones, the receptacle having a central axis,
the body outer surface at least nominally matched to the tapered surface,
the body outer surface and tapered surface configured so that as the body is advanced along the central axis of the receptacle into an operative position within the receptacle, the body outer surface and tapered surface cooperate to cause the central axis of the receptacle and second axis to consistently substantially align,
c) directing the first end of the body into the receptacle to operatively position the body;
d) directing the first fastener through the first opening in the first line into one of the first and second bones; and
e) directing the second fastener through the second opening in the second line into one of the first and second bones,
at least one of the first and second fasteners extending through the ring-shaped inner surface portion and not the second inner surface portion,
at least one of the first and second fasteners directed into one of the first and second bones in a line generally parallel to the central axis of the body.

5. The method of fixing first and second bones according to claim 4 wherein one of the openings is formed so that one of the fasteners is advanced therethrough in one of the first and second lines that is non-parallel to and non-coincident with the central axis of the body.

6. The method of fixing first and second bones according to claim 4 wherein the first and second lines are not parallel to or coincident with each other.

7. The method of fixing first and second bones according to claim 4 wherein the first and second lines are non-parallel to and non-coincident with the central axis of the body.

8. The method of fixing first and second bones according to claim 4 wherein at least a portion of the outer surface of the body has a truncated conical shape.

9. The method of fixing first and second bones according to claim 8 wherein the first end of the body is a leading end as the body is advanced into the operative position, the second end of the body is a trailing end, and the ring-shaped inner surface portion is at the trailing end of the body.

10. The method of fixing first and second bones according to claim 9 wherein the ring-shaped inner surface portion transitions axially into the second inner surface portion.

11. The method of fixing first and second bones according to claim 10 wherein the angle of the ring-shaped inner surface portion to the central axis of the body is greater than an angle at which the second inner surface portion is at relative to the central axis of the body, the diameter of an entire extent of the ring-shaped inner surface greater than the diameter of the second inner surface portion.

12. The method of fixing first and second bones according to claim 10 wherein the second inner surface portion terminates at an axially facing wall.

13. The method of fixing first and second bones according to claim 4 wherein the body has a peripheral wall defining the outer surface and there is at least one discrete receptacle formed in the outer surface to create a volume for bone graft material between the operatively positioned body and one of the bones, the method further comprising the step of directing bone graft material into the at least one discrete receptacle.

14. The method of fixing first and second bones according to claim 4 wherein the central cavity is bounded by a peripheral wall and there is at least one opening through the peripheral wall to allow placement of a volume of bone graft material that is contiguous through the at least one opening between one of the first and second bones and the central cavity, and further comprising the step of placing bone graft material that is contiguous through the at least one opening between one of the first and second bones and central cavity.

15. The method of fixing first and second bones according to claim 14 wherein the at least one opening comprises a plurality of openings, the method further comprising the step of placing the volume of bone graft material that is contiguous through the plurality of openings and central cavity between each of the first and second bones.

16. The method of fixing first and second bones according to claim 4 wherein the body comprises one of: a) a thermoplastic material; and b) a thermoplastic material that is polyether ether ketone (PEEK).

17. The method of fixing first and second bones according to claim 4 wherein the first and second openings each has an entryway that is spaced along the central axis from each of the first and second body ends.

18. The method of fixing first and second bones according to claim 4 wherein the first end of the body is a leading end defined by a leading surface and the second end of the body is a trailing end defined by a trailing surface and the trailing surface has at least a portion thereof that is not perpendicular to the central axis of the body.

19. The method of fixing first and second bones according to claim 4 wherein at least one of the fasteners comprises a polyaxial locking screw.

20. The method of fixing first and second bones according to claim 4 wherein at least one of the fasteners has a head region that is threadably locked to the body.

21. The method of fixing first and second bones according to claim 4 wherein the step of forming a receptacle comprises forming the receptacle using a reamer with a central axis by rotating the reamer around its central axis.

22. The method of fixing first and second bones according to claim 21 wherein the step of forming a receptacle comprises forming the receptacle by removing bone material on each of the first and second bones.

23. The method of fixing first and second bones according to claim 21 wherein the step of forming a receptacle comprises forming the receptacle with a reamer that produces a conical shape for the tapered surface bounding the receptacle.

24. The method of fixing first and second bones according to claim 23 wherein the step of providing an implant comprises providing the implant wherein the outer surface of the body has a conical shape at least nominally matched to the conical shape for the tapered surface bounding the bore.

25. The method of fixing first and second bones according to claim 24 wherein the receptacle has a bottom and the step of directing the first end of the body into the receptacle comprises causing the outer surface of the body to wedge against the tapered surface of the receptacle with the first end of the body spaced from the bottom of the receptacle.

26. The method of fixing first and second bones according to claim 25 further comprising the step of directing one of the fasteners through the first end of the body and into one of the bones and repositioning the one fastener to thereby forcibly draw the outer surface of the body and the tapered surface of the bore against each other.

27. The method of fixing first and second bones according to claim 4 wherein the step of directing the first end of the body into the receptacle comprises pressing the body into the operative position by exerting a force on the body along the central axis of the body and without turning the body around the central axis of the body.

28. The method of fixing first and second bones according to claim 4 wherein the step of providing an implant comprises providing the implant wherein the body has at least one recess at the outer surface to thereby create a volume between the body and one of the first and second bones within the bore and further comprising the step of placing bone graft material in the recess.

29. The method of fixing first and second bones according to claim 4 wherein the step of providing an implant comprises providing the implant wherein the central cavity is bounded by a peripheral wall with an opening through the peripheral wall and further comprising the step of placing bone graft so that a contiguous volume of the bone graft extends from the central cavity through the opening in the peripheral wall and to against one of the bones.

30. The method of fixing first and second bones according to claim 4 wherein the step of providing an implant comprises providing the implant wherein the first and second openings extend through the ring-shaped surface and the steps of directing the first and second fasteners comprise directing the first and second fasteners through the ring-shaped surface along the first and second lines that are non-parallel to and non-coincident with the central axis of the body.

31. A method of fixing first and second bones at a first site, the method comprising the steps of:
   a) providing an implant comprising:
   a body having a central axis and a depth dimension between first and second axially spaced ends,
   the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion,
   a diameter of the ring-shaped inner surface portion greater than a diameter of the second inner surface portion,
   the ring-shaped inner surface portion extending less than one half the depth dimension of the body,
   a plurality of openings in the body each to accept a fastener,
   the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;
   b) forming a receptacle at the first site bounded by a tapered surface at the first site through parts of at least one of the first and second bones, the receptacle having a central axis,
   the body outer surface at least nominally matched to the tapered surface,
   the body outer surface and tapered surface configured so that as the body is advanced along the central axis of the receptacle into an operative position within the receptacle, the body outer surface and tapered surface cooperate to cause the central axis of the receptacle and second axis to consistently substantially align,
   c) directing the first end of the body into the receptacle to operatively position the body;
   d) directing the first fastener through the first opening in the first line into one of the first and second bones; and
   e) directing the second fastener through the second opening in the second line into one of the first and second bones,
   at least one of the first and second fasteners extending through the ring-shaped inner surface portion and not the second inner surface portion,
   wherein the first opening is formed so that the first fastener is advanced into one of the first and second bones in a line substantially parallel to or coincident with the central axis of the body.

32. The method of fixing first and second bones according to claim 31 wherein the second opening is formed so that the second fastener is advanced into one of the first and second bones along the second line that is at an angle to the central axis of the body.

33. A method of fixing first and second bones at a first site, the method comprising the steps of:
   a) providing an implant comprising:
   a body having a central axis and a depth dimension between first and second axially spaced ends,
   the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion, a diameter of the ring-shaped inner surface portion greater than a diameter of the second inner surface portion, the ring-shaped inner surface portion extending less than one half the depth dimension of the body, a plurality of openings in the body each to accept a fastener, the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;

b) forming a receptacle at the first site bounded by a tapered surface at the first site through parts of at least one of the first and second bones, the receptacle having a central axis, the body outer surface at least nominally matched to the tapered surface, the body outer surface and tapered surface configured so that as the body is advanced along the central axis of the receptacle into an operative position within the receptacle, the body outer surface and tapered surface cooperate to cause the central axis of the receptacle and second axis to consistently substantially align, c) directing the first end of the body into the receptacle to operatively position the body;

d) directing the first fastener through the first opening in the first line into one of the first and second bones; and e) directing the second fastener through the second opening in the second line into one of the first and second bones, at least one of the first and second fasteners extending through the ring-shaped inner surface portion and not the second inner surface portion, wherein the step of providing an implant comprises providing the implant wherein the first and second openings extend through the ring-shaped surface and the steps of directing the first and second fasteners comprise directing the first and second fasteners through the ring-shaped surface along the first and second lines that are non-parallel to and non-coincident with the central axis of the body, wherein the step of providing an implant comprises providing the implant wherein the body has a third opening and further comprising the step of directing a third fastener along the central axis of the body through the third opening and into one of the bones.

34. A method of fixing first and second bones at a first site, the method comprising the steps of:

a) providing an implant comprising:

a body having a central axis, a central cavity, and a depth dimension between first and second axially spaced ends, the body having an outer surface with a second axis, a plurality of openings in the body each to accept a fastener, the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;

b) forming a receptacle at the first site bounded by a tapered surface at the first site through parts of the first and second bones, the receptacle having a central axis, the body outer surface at least nominally matched to the tapered surface, the body outer surface and tapered surface configured so that as the body is advanced along the central axis of the receptacle into an operative position within the receptacle, the body outer surface and tapered surface cooperate to cause the central axis of the receptacle and second axis to consistently substantially align;

c) directing the first end of the body into the receptacle to operatively position the body;

d) directing the first fastener through the first opening in the first line into one of the first and second bones; and e) directing the second fastener through the second opening in the second line into one of the first and second bones, wherein at least a portion of the outer surface of the body has a truncated conical shape, wherein the first end of the body is a leading end as the body is advanced into the operative position and the central cavity is bounded by a ring-shaped inner surface portion through which one of the openings is formed, wherein the ring-shaped inner surface portion extends over less than half of the depth dimension between the first and second axial ends of the body and transitions axially into a second inner surface portion that has a shape that is different than a shape of the ring-shaped inner surface portion, one of the first and second fasteners extending through the ring-shaped inner surface portion and not the second inner surface portion, wherein the second inner surface portion terminates at an axially facing wall, wherein one of the openings is formed in the axially facing wall.

35. A method of fixing first and second bones at a first site, the method comprising the steps of:

a) providing an implant comprising:

a body having a central axis and a depth dimension between first and second axially spaced ends, the body having an outer surface with a second axis, a plurality of openings in the body each to accept a fastener, the plurality of openings comprising: i) a first opening through which a first fastener can be directed along a first line that is substantially parallel to or coincident with the central axis of the body and into one of the first and second bones; and ii) a second opening through which a second fastener can be directed along a second line into one of the first and second bones;

b) forming a receptacle at the first site bounded by a tapered surface at the first site through parts of the first and second bones, the receptacle having a central axis, the body outer surface at least nominally matched to the tapered surface, the body outer surface and tapered surface configured so that as the body is advanced along the central axis of the receptacle into an operative position within the receptacle, the body outer surface and tapered surface cooperate to cause the central axis of the receptacle and second axis to consistently substantially align;

c) directing the first end of the body into the receptacle;

d) directing the first fastener through the first opening into one of the first and second bones; and e) directing the second fastener through the second opening into the other one of the first and second bones, wherein the body has an axially facing wall and the first opening is on the axially facing wall, the implant and first and second fasteners configured so that with the second fastener directed through the second opening into the other one of the first and second bones, direction of the first fastener through the first opening into the one of the first and second bones causes the one of the first and second bones to be drawn along the central axis of the body toward the other one of the first and second bones.

36. The method of fixing first and second bones according to claim 35 wherein the first opening is unthreaded.

37. A method of fixing first and second bones at a first site, the method comprising the steps of:
a) providing an implant comprising:
a body having a central axis and a depth dimension between first and second axially spaced ends,
the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion,
a diameter of the ring-shaped inner surface portion greater than a diameter of the second inner surface portion,
the ring-shaped inner surface portion extending less than one half the depth dimension of the body,
a plurality of openings in the body each to accept a fastener,
the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;
b) forming a receptacle at the first site bounded by a tapered surface at the first site through parts of at least one of the first and second bones, the receptacle having a central axis,
the body outer surface at least nominally matched to the tapered surface,
the body outer surface and tapered surface configured so that as the body is advanced along the central axis of the receptacle into an operative position within the receptacle, the body outer surface and tapered surface cooperate to cause the central axis of the receptacle and second axis to consistently substantially align,
c) directing the first end of the body into the receptacle to operatively position the body;
d) directing the first fastener through the first opening in the first line into one of the first and second bones; and
e) directing the second fastener through the second opening in the second line into one of the first and second bones,
at least one of the first and second fasteners extending through the ring-shaped inner surface portion and not the second inner surface portion,
wherein the body has a peripheral wall and the peripheral wall has a discrete truncation extending only partially around the central axis at the first end, the truncation defining a flat surface that is non-orthogonal to the central axis.

38. A method of fixing first and second bones at a first site, the method comprising the steps of:
a) providing an implant comprising:
a body having a central axis and a depth dimension between first and second axially spaced ends,
the body having an outer surface with a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion,
a diameter of the ring-shaped inner surface portion greater than a diameter of the second inner surface portion,
a plurality of openings in the body each to accept a fastener,
the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;
b) forming a receptacle at the first site bounded by a tapered surface at the first site through parts of at least one of the first and second bones, the receptacle having a central axis,
the body outer surface at least nominally matched to the tapered surface,
the body outer surface and tapered surface configured so that as the body is advanced along the central axis of the receptacle into an operative position within the receptacle, the body outer surface and tapered surface cooperate to cause the central axis of the receptacle and second axis to consistently substantially align,
c) directing the first end of the body into the receptacle to operatively position the body;
d) directing the first fastener through the first opening in the first line into one of the first and second bones; and
e) directing the second fastener through the second opening in the second line into one of the first and second bones,
at least one of the first and second fasteners extending through the ring-shaped inner surface portion,
wherein the body has a peripheral wall and the peripheral wall has a discrete truncation extending only partially around the central axis at the first end, the truncation defining a flat surface that is non-orthogonal to the central axis.

39. A method of fixing first and second bones at a first site, the method comprising the steps of:
providing an implant comprising:
a) a body having a central axis and a depth dimension between first and second axially spaced ends,
the body having an outer surface with a second axis,
a plurality of openings in the body each to accept a fastener,
the plurality of openings comprising: i) a first opening through which a first fastener can be directed along a first line that is substantially parallel to or coincident with the central axis of the body and into one of the first and second bones; and ii) a second opening through which a second fastener can be directed along a second line into one of the first and second bones;
b) forming a receptacle at the first site bounded by a tapered surface at the first site through parts of at least one of the first and second bones, the receptacle having a central axis;
the body outer surface at least nominally matched to the tapered surface,
the body outer surface and tapered surface configured so that as the body is advanced along the central axis of the receptacle into an operative position within the receptacle, the body outer surface and tapered surface cooperate to cause the central axis of the receptacle and second axis to consistently substantially align, c) directing the first end of the body into the receptacle;

d) directing the first fastener through the first opening along the first line into one of the first and second bones; and e) directing the second fastener through the second opening along the second line into one of the first and second bones, wherein the step of forming a receptacle comprises forming a receptacle at the patient's sinus tarsi.

40. The method of fixing first and second bones according to claim 39 wherein the second line is at an angle to the first line.

41. The method of fixing first and second bones according to claim 39 wherein the body has a central cavity bounded by a peripheral wall and there is at least one opening through the peripheral wall to allow placement of a volume of bone graft material through the at least one opening between one of the first and second bones and the central cavity, the method further comprising the step of placing the volume of bone graft through the at least one opening between the one of the first and second bones and central cavity.

42. The method of fixing first and second bones according to claim 39 wherein the body has a peripheral wall defining the outer surface and there is at least one discrete receptacle formed in the outer surface to create a localized volume for bone graft material between the operatively positioned body and one of the bones, the method further comprising the step of placing a volume of bone graft material into the at least one discrete receptacle.

43. The method of fixing first and second bones according to claim 39 wherein the step of forming a receptacle comprises forming the receptacle using a reamer with a central axis by rotating the reamer around its central axis.

44. The method of fixing first and second bones according to claim 39 wherein the implant and first and second fasteners are configured so that with the second fastener directed through the second opening into the other one of the first and second bones, direction of the first fastener through the first opening into the one of the first and second bones causes the one of the first and second bones to be drawn along the central axis of the body toward the other one of the first and second bones.

45. The method of fixing first and second bones according to claim 44 wherein the body has an axially facing wall and the first opening extends through the axially facing wall.

46. A method of fixing first and second bones at a first site, the method comprising the steps of:

a) providing an implant comprising:

a body having a central axis and a depth dimension between first and second axially spaced ends, the body having an outer surface with a fixed shape and diameter around a second axis and a central cavity bounded by a ring-shaped inner surface portion that is at an angle to the central axis of the body, the central cavity having a second inner surface portion axially spaced from the ring-shaped inner surface portion and having a shape that is different than a shape of the ring-shaped inner surface portion, a diameter of the ring-shaped inner surface portion greater than a diameter of the second inner surface portion, the ring-shaped inner surface portion extending less than one half the depth dimension of the body, a plurality of openings in the body each to accept a fastener, the plurality of openings comprising: i) a first opening through which a first fastener can be directed along a first line through the operatively positioned body and into one of the first and second bones; and ii) a second opening through which a second fastener can be directed along a second line through the operatively positioned body and into one of the first and second bones;

b) forming a receptacle at the first site bounded by a tapered surface at the first site through parts of at least one of the first and second bones, the receptacle having a central axis, the body outer surface at least nominally matched to the tapered surface, the body outer surface and tapered surface configured so that as the body is advanced along the central axis of the receptacle into an operative position within the receptacle, the body outer surface and tapered surface cooperate to cause the central axis of the receptacle and second axis to consistently substantially align, c) directing the first end of the body into the receptacle to operatively position the body;

d) directing the first fastener through the first opening in the first line into one of the first and second bones; and e) directing the second fastener through the second opening in the second line into one of the first and second bones, at least one of the first and second fasteners extending through the ring-shaped inner surface portion and not the second inner surface portion, wherein the first and second bones are a patient's talus and calcaneus bones.

47. The method of fixing first and second bones according to claim 46 wherein the step of forming a receptacle comprises forming the receptacle at the patient's sinus tarsi.

* * * * *